United States Patent
Nagai et al.

(10) Patent No.: US 12,351,866 B2
(45) Date of Patent: Jul. 8, 2025

(54) NUCLEIC ACID AMPLIFICATION METHOD

(71) Applicants: NATIONAL INSTITUTE OF ADVANCED INDUSTRIAL SCIENCE AND TECHNOLOGY, Tokyo (JP); KYORIN PHARMACEUTICAL CO., LTD., Tokyo (JP)

(72) Inventors: Hidenori Nagai, Ikeda (JP); Satoru Iwanami, Tokyo (JP)

(73) Assignees: NATIONAL INSTITUTE OF ADVANCED INDUSTRIAL SCIENCE AND TECHNOLOGY, Tokyo (JP); KYORIN PHARMACEUTICAL CO., LTD., Tokyo (JP)

(*) Notice: Subject to any disclaimer, the term of this patent is extended or adjusted under 35 U.S.C. 154(b) by 938 days.

(21) Appl. No.: 17/438,012

(22) PCT Filed: Mar. 13, 2020

(86) PCT No.: PCT/JP2020/011249
§ 371 (c)(1),
(2) Date: Sep. 10, 2021

(87) PCT Pub. No.: WO2020/189581
PCT Pub. Date: Sep. 24, 2020

(65) Prior Publication Data
US 2022/0145360 A1 May 12, 2022

(30) Foreign Application Priority Data
Mar. 15, 2019 (JP) .................. 2019-049009

(51) Int. Cl.
*C12Q 1/686* (2018.01)
*B01L 7/00* (2006.01)

(52) U.S. Cl.
CPC .............. *C12Q 1/686* (2013.01); *B01L 7/525* (2013.01)

(58) Field of Classification Search
CPC ..................................... C12Q 1/686
See application file for complete search history.

(56) References Cited

U.S. PATENT DOCUMENTS

| 6,699,661 B1 | 3/2004 | Kurane et al. |
| 2001/0000148 A1 | 4/2001 | Kurane et al. |

(Continued)

FOREIGN PATENT DOCUMENTS

| JP | 2004-305219 A | 11/2004 |
| JP | 2009-517075 A | 4/2009 |

(Continued)

OTHER PUBLICATIONS

Furutani et al. Development of an on-site rapid real-time polymerase chain reaction system and the characterization of suitable DNA polymerases for TaqMan probe technology. Anal Bioanal Chem 408, 5641-564 (Year: 2016).*

(Continued)

*Primary Examiner* — Aaron A Priest
*Assistant Examiner* — Tian Yu
(74) *Attorney, Agent, or Firm* — Leydig, Voit & Mayer, Ltd.

(57) ABSTRACT

The invention provides a reciprocal-flow-type nucleic acid amplification method performing thermal cycling by reciprocating a sample liquid between a denaturation temperature zone and an elongation-annealing temperature zone with a connected microchannel including at least a curved channel corresponding to the denaturation temperature zone, a curved channel corresponding to the elongation-annealing temperature zone, a linear or curved intermediate channel that connects the aforementioned curved channels, and a (Continued)

connector to connect to a liquid delivery mechanism for enabling movement of the sample liquid. The method includes moving the sample liquid in the channel by the liquid delivery mechanism that is open to atmospheric pressure when liquid delivery is stopped, and measuring a fluorescence intensity for each thermal cycle at a predetermined point on the channel corresponding to the denaturation temperature zone and at a predetermined point on the channel corresponding to the elongation-annealing temperature zone to perform real-time PCR.

6 Claims, 3 Drawing Sheets

Specification includes a Sequence Listing.

(56) References Cited

U.S. PATENT DOCUMENTS

| | | |
|---|---|---|
| 2001/0000175 A1 | 4/2001 | Kurane et al. |
| 2003/0082592 A1 | 5/2003 | Kurane et al. |
| 2004/0063137 A1 | 4/2004 | Kurane et al. |
| 2006/0177856 A1 | 8/2006 | Kurane et al. |
| 2009/0148933 A1 | 6/2009 | Battrell et al. |
| 2017/0130261 A1* | 5/2017 | Nagai .................. C12N 15/09 |
| 2018/0274019 A1 | 9/2018 | Fukuzawa et al. |
| 2018/0311673 A1 | 11/2018 | Fukuzawa et al. |
| 2019/0255525 A1 | 8/2019 | Fukuzawa |
| 2020/0086313 A1 | 3/2020 | Fukuzawa et al. |
| 2020/0139371 A1 | 5/2020 | Fukuzawa et al. |
| 2020/0157607 A1 | 5/2020 | Nagai et al. |
| 2021/0178091 A1 | 6/2021 | Duc et al. |

FOREIGN PATENT DOCUMENTS

| | | |
|---|---|---|
| WO | WO 2007/063347 A1 | 6/2007 |
| WO | WO 2008/147382 A1 | 12/2008 |
| WO | WO 2016/006612 A1 | 1/2016 |
| WO | 2018/084017 A1 | 5/2018 |
| WO | WO 2018/225577 A1 | 12/2018 |
| WO | WO 2018/235766 A1 | 12/2018 |

OTHER PUBLICATIONS

Chen et al. Ultrasensitive PCR and real-time detection from human genomic samples using a bidirectional flow microreactor. Anal Chem. Dec. 1, 2007;79(23):9185-90. doi: 10.1021/ac701668k. Epub Nov. 3, 2007. PMID: 17979297 (Year: 2007).*

Furutani et al. Development of an on-site rapid real-time polymerase chain reaction system and the characterization of suitable DNA polymerases for TaqMan probe technology. Anal Bioanal Chem 408, 5641-5649 (2016) (Year: 2016).*

Ultrasensitive PCR and real-time detection from human genomic samples using a bidirectional flow microreactor. Anal Chem. Dec. 1, 2007;79(23):9185-90. doi: 10.1021/ac701668k. Epub Nov. 3, 2007. PMID: 17979297 (Year: 2007).*

Chiou et al., "A Closed-Cycle Capillary Polymerase Chain Reaction Machine," *Anal. Chem.*, 73(9): 2018-2021 (2001).

Japanese Patent Office, International Search Report in International Patent Application No. PCT/JP2020/011249 (Jun. 16, 2020).

Japan Patent Office, Decision of Refusal in Japanese Patent Application No. 2021-507320 (Mar. 18, 2025).

* cited by examiner

SEQUENCE LISTING

```
<160> NUMBER OF SEQ ID NOS: 9

<210> SEQ ID NO 1
<211> LENGTH: 26
<212> TYPE: DNA
<213> ORGANISM: Streptococcus pneumoniae
```

```
<400> SEQUENCE: 1
aactcttacg caatctagca gatgaa                                          26

<210> SEQ ID NO 2
<211> LENGTH: 22
<212> TYPE: DNA
<213> ORGANISM: Streptococcus pneumoniae

<400> SEQUENCE: 2
cgtgcaatac tcgtgcgttt ta                                              22

<210> SEQ ID NO 3
<211> LENGTH: 18
<212> TYPE: DNA
<213> ORGANISM: Streptococcus pneumoniae

<400> SEQUENCE: 3
ccgaaaacgc ttgataca                                                   18

<210> SEQ ID NO 4
<211> LENGTH: 22
<212> TYPE: DNA
<213> ORGANISM: Haemophilus influenzae

<400> SEQUENCE: 4
ggaatcccaa tgcacaagaa ca                                              22

<210> SEQ ID NO 5
<211> LENGTH: 23
<212> TYPE: DNA
<213> ORGANISM: Haemophilus influenzae

<400> SEQUENCE: 5
gctttggtca acacatcaac ctt                                             23

<210> SEQ ID NO 6
<211> LENGTH: 20
<212> TYPE: DNA
<213> ORGANISM: Haemophilus influenzae

<400> SEQUENCE: 6
cattattagt tgcaggttct                                                 20

<210> SEQ ID NO 7
<211> LENGTH: 33
<212> TYPE: DNA
<213> ORGANISM: Mycoplasma pneumoniae

<400> SEQUENCE: 7
cttggtctcc atacttaact aaataaaaaa ctc                                  33

<210> SEQ ID NO 8
<211> LENGTH: 22
<212> TYPE: DNA
<213> ORGANISM: Mycoplasma pneumonia

<400> SEQUENCE: 8
gaactacaag ccgctaatgc ag                                              22

<210> SEQ ID NO 9
<211> LENGTH: 24
<212> TYPE: DNA
<213> ORGANISM: Mycoplasma pneumoniae
```

```
<400> SEQUENCE: 9
gccttgaagg ctgggtttgc gcta                                              24
```

NUCLEIC ACID AMPLIFICATION METHOD

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,777 bytes ASCII (Text) file named "757330SequenceListing.txt," created Sep. 9, 2021.

CROSS-REFERENCE TO RELATED PATENT APPLICATION

Technical Field

The present application claims priority to Japanese Patent Application No. 2019-049009, filed on Mar. 15, 2019, the entire contents of which is herein incorporated by reference. The present invention relates to a nucleic acid amplification method.

Background Art

Nucleic acid detection is central core in a variety of areas, including drug research and development, forensic medicine, clinical inspection, and identification of the species of crops and pathogenic microorganisms. The ability to detect various diseases (e.g., cancer), microbial infections, and genetic markers through molecular phylogenetic analysis is a universal technology for the diagnosis of diseases and risk of developing, marker search, safety assessment of food and environment, proof of crime, and many other techniques.

One of the most powerful basic technologies for detecting a small amount of nucleic acid (a gene) with high sensitivity is analyzing a product obtained by exponentially replicating and amplifying a portion of a nucleic acid sequence, or the entire sequence.

Polymerase chain reaction (PCR) is a powerful technique for selectively amplifying a specific region of DNA. PCR can be used to generate millions of copies of a DNA fragment from a single template DNA, for a targeted DNA sequence in the template DNA. PCR repeatedly uses three-phase or two-phase temperature conditions called thermal cycling to sequentially repeat the individual reactions of denaturation of DNA to single strands, annealing of primers to the denatured DNA single strands, and extension of the primers by thermally stable DNA polymerases. This cycle is repeated until a sufficient number of copies are obtained for analysis. In principle, the number of copies can be doubled in a single cycle of PCR. In reality, as thermal cycling continues, the concentration of necessary reaction reagents decreases; thus, the accumulation of amplified DNA products eventually ends. For general details of PCR, see Clinical Applications of PCR, Dennis Lo (ed.), Humana Press (Totowa, NJ, 1998); and PCR Protocols: A Guide to Methods and Applications, M. A. Innis et al. (eds.), Academic Press Inc. (San Diego, CA, 1990).

Although PCR is a powerful technique capable of selectively amplifying target DNA, the amplified DNA must be confirmed by separately performing another operation, such as gel electrophoresis, after PCR is completed. To improve PCR, real-time PCR was developed that generates or quenches fluorescence according to the amount of amplified target DNA. Real-time PCR has simplified the confirmation as to whether target DNA is present in a sample. In the conventional PCR techniques, template DNA in a pre-PCR sample exceeding a predetermined amount often results in the amount of amplified post-PCR DNA reaching a plateau; this hampers the quantification of the amount of pre-PCR template DNA. However, real-time PCR enables real-time detection of the amount of amplified DNA during PCR before the amount of amplified DNA reaches a plateau; thus, the amount of pre-PCR template DNA can be quantified from the progress of DNA amplification. This is why real-time PCR is also called "quantitative PCR."

Quantification of the amount of target DNA by real-time PCR is particularly useful in clinical practice, for example, in monitoring the change in viral levels to confirm the efficacy of treatment of viral infections, such as the AIDS virus (HIV). DNA quantification by real-time PCR is also effective in the diagnosis of opportunistic infections such as of herpes viruses (HHV), with which many are often subclinically infected since early childhood, and then develop the infection due to the proliferation of viruses when physically weakened.

Although PCR and real-time PCR are powerful techniques for exponentially amplifying genes by thermal cycling, conventional thermal cyclers used in PCR are slow in temperature control due to the massive heat capacity of the aluminum block used as a heater; and conventionally take 1 to 2 hours, or even more in some cases, to perform 30 to 40 cycles of PCR. Thus, even with the use of state-of-the-art genetic testing devices, analysis usually takes more than one hour in total. Speeding up the PCR operation has been a great challenge since the advent of the technique.

The inventors of the present invention developed a reciprocal-flow-type nucleic acid amplification device that uses a microblower or like equipment as a liquid delivery mechanism, with the aim of speeding up the PCR operation (PTL 1).

In the meantime, multiplex PCR, which amplifies multiple gene regions simultaneously by using multiple primer pairs in a single PCR reaction system, has been attracting attention. Real-time multiplex PCR, which is more advanced multiplex PCR, aims to distinguish and detect multiple different target genes and to obtain quantitative results, while being less affected by other targets (crosstalk) without reducing sensitivity. However, a quantitative multiplex reaction of two or more targets has been reported as often being difficult due to the problems such as the limited combination of fluorescent substances usable for labelling to avoid the overlap of fluorescence wavelengths.

PTL 1 reports the results of measurement at one point on a linear channel of a microchannel (a detection point) by using a multicolor fluorescence detector capable of simultaneously measuring three types of fluorescence as an example of multiplex PCR.

CITATION LIST

Patent Literature

PTL 1: WO2016/006612A

SUMMARY OF INVENTION

Technical Problem

However, if the fluorescence intensity of multiple probes is simultaneously measured at one detection point on a linear channel by using a multicolor fluorescence detector in multiplex PCR as in PTL 1, the spectrum of the fluorescence wavelength emitted from one of the probes overlaps in part with the spectrum of the fluorescence wavelength from another probe measured simultaneously or the spectrum of the wavelength of the light source used to excite a fluorescence dye labelling other probes, and these spectra cannot be distinguished from one another. Thus, in order to accurately measure the fluorescence intensity, it is desirable to have no such interference between fluorescence emissions, or between fluorescence emissions and excitation light.

In order to prevent such interference, three measurement points can be arranged on a linear channel, and the excitation light source can be switched on at different times with time lags to measure the fluorescence intensity. Inconveniently, however, the liquid delivery speed must be slowed down to avoid interference.

An object of the present invention is to provide a real-time PCR method that is fast with reduced noise, even in performing multiplex PCR.

Solution to Problem

After conducting extensive research to achieve the above object, the inventors found that the object can be achieved by measuring the fluorescence intensity for each thermal cycle at predetermined points in two spatially separated temperature zones in a microchannel when performing real-time PCR. The inventors conducted further research on the basis of this finding, and completed the present invention.

The present invention includes the following embodiments.

Item 1.

A reciprocal-flow-type nucleic acid amplification method performing thermal cycling by reciprocating a sample liquid between two spatially separated temperature zones in a microchannel that connects the two temperature zones, wherein
  the two temperature zones are a denaturation temperature zone and an elongation-annealing temperature zone,
  the microchannel includes at least
    a curved channel corresponding to the denaturation temperature zone,
    a curved channel corresponding to the elongation-annealing temperature zone,
    a linear or curved intermediate channel that connects the curved channel corresponding to the denaturation temperature zone and the curved channel corresponding to the elongation-annealing temperature zone, and
    a connector connectable to a liquid delivery mechanism for enabling movement of the sample liquid,
  the method comprising
    moving the sample liquid in the microchannel by the liquid delivery mechanism that is open to atmospheric pressure when liquid delivery is stopped, and
    measuring a fluorescence intensity for each thermal cycle at a predetermined point on the channel corresponding to the denaturation temperature zone and at a predetermined point on the channel corresponding to the elongation-annealing temperature zone to perform real-time PCR.

Item 2.

A nucleic acid amplification method comprising the following steps:
  step 1 of mounting a chip for nucleic acid amplification on a substrate of a reciprocal-flow-type nucleic acid amplification device being capable of performing real-time PCR by measuring fluorescence intensity for each thermal cycle,
    the reciprocal-flow-type nucleic acid amplification device including
      a heater to form a denaturation temperature zone and an elongation-annealing temperature zone,
      a fluorescence detector to measure a fluorescence intensity of a sample liquid present in the denaturation temperature zone,
      a fluorescence detector to measure a fluorescence intensity of the sample liquid present in the elongation-annealing temperature zone,
      a liquid delivery mechanism to allow the sample liquid to move between the denaturation temperature zone and the elongation-annealing temperature zone, and to become open to atmospheric pressure when liquid delivery is stopped,
      the substrate on which the chip for nucleic acid amplification is mounted, and
      a control mechanism to receive an electric signal related to the movement of the sample liquid from the fluorescence detector to control the drive of the liquid delivery mechanism,
    the chip for nucleic acid amplification including at least one microchannel, the at least one microchannel including
      a curved channel corresponding to the denaturation temperature zone,
      a curved channel corresponding to the elongation-annealing temperature zone,
      a linear or curved intermediate channel that connects the curved channel corresponding to the denaturation temperature zone and the curved channel corresponding to the elongation-annealing temperature zone, and
      a connector to connect the liquid delivery mechanism of the nucleic acid amplification device to one or both ends of the microchannel;
  step 2 of connecting the connector for the liquid delivery mechanism in the microchannel to the liquid delivery mechanism;
  step 3 of reciprocating the sample liquid between the two curved channels in the microchannel by the liquid delivery mechanism to perform thermal cycling; and
  step 4 of measuring a fluorescence intensity of the sample liquid for each thermal cycle at a predetermined point on the curved channel corresponding to the denaturation temperature zone and at a predetermined point on the curved channel corresponding to the elongation-annealing temperature zone by the fluorescence detectors.

Item 3.

The nucleic acid amplification method according to Item 1 or 2, wherein the liquid delivery mechanism is a microblower or fan.

Item 4.

The nucleic acid amplification method according to any one of Items 1 to 3, wherein the intermediate channel that connects the curved channels is a linear channel.

Item 5.

The nucleic acid amplification method according to Item 4, wherein the reciprocal-flow-type nucleic acid amplification device further includes a fluorescence detector to measure a fluorescence intensity of the sample liquid that passes through the intermediate channel that connects the curved channel corresponding to the denaturation temperature zone and the curved channel corresponding to the elongation-annealing temperature zone, the method comprising the step of measuring a fluorescence intensity of the sample liquid for each thermal cycle at a predetermined point on the intermediate channel by the fluorescence detector.

Item 6.

The nucleic acid amplification method according to Item 5, wherein a distance between a fluorescence measurement point (P2) on the intermediate channel and a fluorescence measurement point (P1) on the denaturation temperature zone is 8 mm or more.

Advantageous Effects of Invention

The present invention provides a real-time PCR method that is fast with reduced noise, even in performing multiplex PCR.

DESCRIPTION OF EMBODIMENTS

Figure 1:
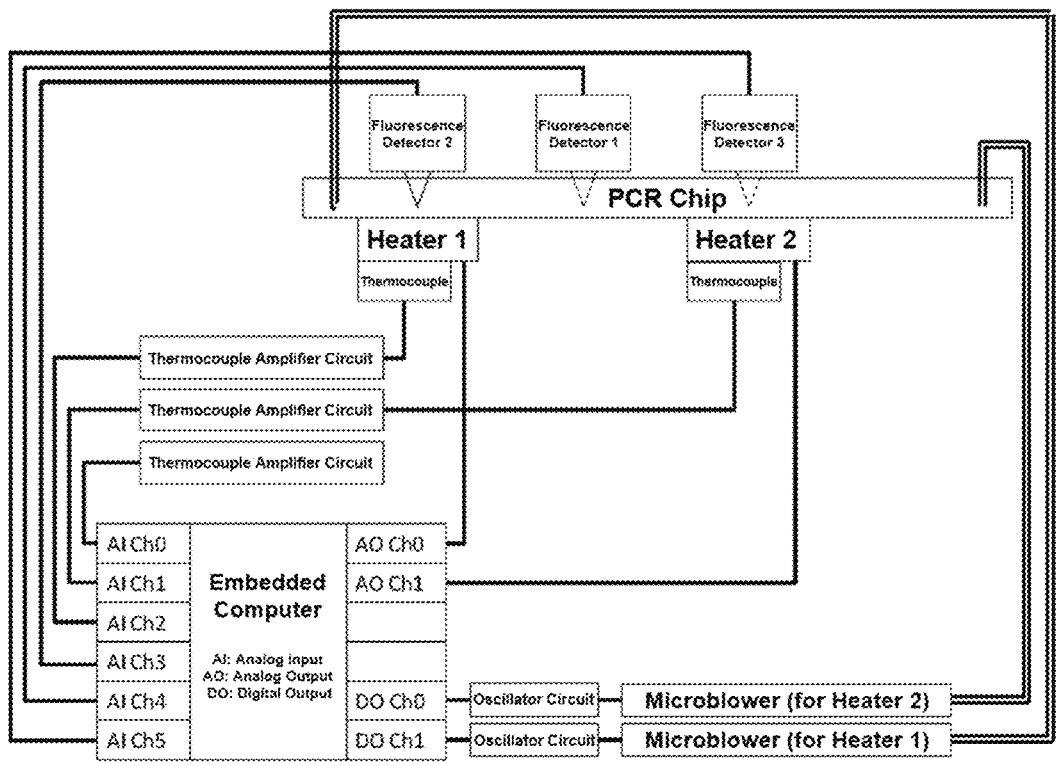
FIG. 1 shows an example of the structure of a nucleic acid amplification device (two heaters).

The nucleic acid amplification method according to the present invention is described in detail below.

The nucleic acid amplification method according to the present invention performs thermal cycling by allowing a sample liquid to reciprocate between two temperature zones in a microchannel. This type of nucleic acid amplification method is sometimes referred to as a "reciprocal-flow-type nucleic acid amplification method."

Of the PCR (polymerase chain reactions) techniques, the nucleic acid amplification method according to the present invention is real-time PCR capable of monitoring the status of gene amplification during a PCR reaction. PCR amplifies a nucleic acid by using multiple cycles of denaturation, annealing of primer pairs to opposing strands, and primer extension that results in an exponential increase in the number of copies of a target nucleic acid sequence.

To achieve real-time PCR, fluorescence intensity is measured for each thermal cycle. Specifically, the initial amount of target DNA can be quantified by recording the changes in fluorescence intensity over time for each cycle, which increases as the target DNA is amplified by thermal cycling, and calculating the number of cycles (Ct value) at which the fluorescence intensity exceeds the threshold. In PCR, the manner of gene amplification (i.e., the number of cycles at which a gene product logarithmically increases) depends on the amount of the base template. Thus, the amount of the target gene present in a sample can be calculated by comparing the amplification of the gene with that of an external standard DNA with a known concentration.

The nucleic acid amplification method according to the present invention may be performed with either DNA or RNA as a template. With DNA as a template, PCR is performed by using the nucleic acid amplification device as configured in FIG. 1. With RNA as a template (real-time RT-PCR), complementary DNA (cDNA) is first generated (reverse transcription) from mRNA by reverse transcriptase by using the nucleic acid amplification device as configured in FIG. 2, and then PCR is performed. The kit and protocol for use in PCR can be selected from a range of known kits and protocols. When the nucleic acid amplification method according to the present invention is real-time RT-PCR, One-Step RT-PCR can be used, which enables quick and simple reverse transcription and cycling in PCR in one step.

In a preferable embodiment, the nucleic acid amplification method according to the present invention is multiplex PCR that amplifies multiple gene regions simultaneously by using multiple primer pairs in a single PCR reaction system. The nucleic acid amplification method according to the present invention is particularly preferably multiplex PCR that amplifies two or three different gene regions simultaneously.

The nucleic acid amplification method according to the present invention is performed by allowing a sample liquid to move through a microchannel. The microchannel for performing the nucleic acid amplification method according to the present invention includes at least a curved channel corresponding to a denaturation temperature zone, a curved channel corresponding to an elongation-annealing temperature zone, a linear or curved intermediate channel that connects the curved channel corresponding to the denaturation temperature zone and the curved channel corresponding to the elongation-annealing temperature zone, and a connector to connect to a liquid delivery mechanism that enables the movement of a sample liquid. The microchannel may also include an opening for introducing the sample liquid. The opening for introducing the sample liquid can be sealed by an optionally selected seal, valve, or like component.

The microchannel is preferably famed of a material that satisfies some or all of the following requirements: (i) relatively high thermal conductivity, (ii) stability over the temperature range required for PCR, (iii) resistance to erosion caused by electrolyte solutions or organic solvents, and (iv) low adsorption of nucleic acids and proteins. Specific examples of materials include glass, quartz, silicon and a variety of thermosetting or photo-curable resins, such as cycloolefin polymers (COP). From the standpoint of detecting fluorescence, the material preferably has a high permeability of light (in particular, excitation light and emitted light for performing fluorescence detection) (i.e., the material does not absorb, diffuse, or reflect much light), and is transparent.

The microchannel may have a structure in which grooves are formed in the material by, for example, symachine processing such as NC machining cutting, injection molding, nanoimprinting, or soft lithography; and in which the grooves are sealed by a seal (preferably a transparent seal famed of, for example, polyolefin). Alternatively, the microchannel can be formed by three-dimensional printing. The cross-section of the microchannel can be of any shape; and the shape may be, for example, semicircular, circular, rectangular, wedge-shaped, trapezoidal, or polygonal. The cross-section of the microchannel can be, for example, about 10 to 1000 μm wide and about 10 to 1000 μm deep. The width and depth of the microchannel can be constant, or the width or depth can be partially varied.

The curved channel corresponding to the denaturation temperature zone and the curved channel corresponding to the elongation-annealing temperature zone in the microchannel can be a serpentine microchannel with a loop shape, or a spiral curved microchannel. The intermediate channel that connects the curved channel corresponding to the denaturation temperature zone to the curved channel corresponding to the elongation-annealing temperature zone can be of a linear or curved shape.

The curved channel corresponding to the denaturation temperature zone and the curved channel corresponding to the elongation-annealing temperature zone each preferably have a length of 20 mm or more.

The curved channel corresponding to the denaturation temperature zone and the curved channel corresponding to the elongation-annealing temperature zone in the microchannel are each maintained at a predetermined temperature. The temperature of the sample liquid delivered to the temperature zones is changed to the temperature of the temperature zones.

The denaturation temperature zone is maintained at a temperature required for the DNA denaturation reaction in PCR. The temperature of the denaturation temperature zone is preferably about 90 to 100° C., and more preferably about 95° C. The elongation-annealing temperature zone is maintained at a temperature required for the annealing and elongation reactions of DNA in PCR. The temperature in the elongation-annealing temperature zone is preferably about 40 to 75° C., and more preferably about 55 to 65° C.

The denaturation temperature zone and the elongation-annealing temperature zone are each preferably maintained at a constant temperature. The maintenance of temperature can be achieved by a heat source. The heat source is, for example, built into or in contact with the microchannel. Specific examples of heat sources include a cartridge heater, a film heater, and a Peltier heater.

In the nucleic acid amplification method according to the present invention, the sample liquid, in a plugged form, flows through the microchannel. The sample liquid flowing through the microchannel can be of any volume, and is preferably about 5 to 50 µL, and more preferably about 15 to 20 µL.

The sample liquid contains the components necessary for PCR reaction and the components necessary for fluorescence detection to enable real-time PCR. For example, the sample liquid contains an aqueous medium mainly composed of water, enzymes such as a template nucleic acid (either DNA or RNA) polymerase, and a reverse transcriptase, optionally labeled deoxyribonucleotide triphosphates, and primer sets for corresponding target gene regions as components necessary for PCR reaction; and fluorescent probes (e.g., TaqMan probe, Cycleave probe, E-probe (registered trademark)), and dyes (e.g., SYBR GREEN) as components necessary for fluorescence detection. The sample liquid may contain a buffer component to adjust the pH and salt concentration.

When the PCR of the present invention is multiplex PCR, the sample liquid contains two or more types of primer sets. In general, "primer set" refers to a combination of a forward primer and a reverse primer; typically, one type of a forward primer and one type of a reverse primer are used for one target gene region. Even if the primer set of the present invention contains only one reverse primer and can generate amplification products corresponding to respective gene regions, in combination with two or more forward primers (as a primer pair), the primer set can be used as a primer set for multiplex PCR.

Examples of dyes (fluorescent dyes) for use in fluorescence detection include ABY, acridine, Alexa Fluor 488, Alexa Fluor 532, Alexa Fluor 594, Alexa Fluor 633, Alexa Fluor 647, ATTO (ATTO-TEC fluorescent dye), Biosearch Blue, Cy3, Cy3.5, Cy5, Cy5.5, coumarin, DANSYL, FAM (e.g., 5-FAM, 6-FAM), FITC, GPF, 5-HEX, 6-HEX, JOE, JUN, Marina Blue, NED, Oregon Green 488, Oregon Green 500, Oregon Green 514, Pacific Blue, PET, Pulsar, Quasar 570, Quasar 670, Quasar 705, Rhodamine Green, Rhodamine Red, 5-ROX, 6-ROX, 5-TAMRA, 6-TAMRA, 5-TET, 6-TET, Texas Red, TRITC, and VIC.

The dye for use in multiplex PCR in the present invention preferably contains at least one member selected from the group consisting of ABY and HEX, such as a combination of ABY, Cy5, and FAM; and a combination of HEX, Cy5, and FAM.

The movement of the sample liquid in the nucleic acid amplification method according to the present invention is achieved by a liquid delivery mechanism that is open to atmospheric pressure when liquid delivery is stopped. Specifically, instead of using a mechanism that requires to form the inside of the channel as a closed system to prevent pressure from escaping (e.g., a syringe pump), the present invention uses a liquid delivery mechanism configured to form an open system even during liquid delivery. Such a liquid delivery mechanism causes the pressure inside the channel to instantly become equal to the pressure outside the channel at the time airflow stops, and eliminates the pressure acting on the plugged sample liquid, thus immediately stopping liquid delivery. This enables precision position control without multiple pressure-relief valves for controlling the position of the sample liquid.

Examples of liquid delivery mechanisms that are open to atmospheric pressure when liquid delivery stops include a microblower, and a fan.

A microblower, which is also referred to as a "piezoelectric microblower," is a known device that draws and ejects air, and is characterized by its non-sealed structure (without a non-return valve). A typical microblower bends and deforms its diaphragm by a voltage applied to a piezoelectric element to draw and eject air. For example, microblowers manufactured by Murata Manufacturing Co., Ltd (MZB1001T02, MZB3004T04) can be used.

A fan refers to a device that blows air by the rotating motion of an impeller. Due to the structural characteristics of the impeller, the channel is not formed into a closed system.

In the nucleic acid amplification method according to the present invention, reciprocal-flow-type nucleic acid amplification is performed by the following [1] to [4] as one cycle:

[1] The step of operating the liquid delivery mechanism to move the sample liquid from the elongation-annealing temperature zone to the denaturation temperature zone through the intermediate channel,

[2] The step of stopping the liquid delivery mechanism to retain the sample liquid in the denaturation temperature zone for a predetermined period of time,

[3] The step of operating the liquid delivery mechanism to move the sample liquid from the denaturation temperature zone to the elongation-annealing temperature zone through the intermediate channel, and

[4] The step of operating the liquid delivery mechanism to retain the sample liquid in the elongation-annealing temperature zone for a predetermined period of time.

This cycle is performed at least one time, preferably about 30 to 50 times, and more preferably about 35 to 50 times to perform thermal cycling. The number of cycles can be suitably determined according to the concentration of the template nucleic acid, the type of target genes, etc.

In the nucleic acid amplification method according to the present invention, the speed of sample liquid movement, in particular the speed at which the sample liquid flows through the intermediate channel, can be, for example, about 25 mm/second to 2.2 m/second, more preferably about 40 mm/second to 1 m/second, or about 60 mm/second to 300 mm/second.

The period of time during which the sample liquid is retained in the denaturation temperature zone and the period of time during which the sample liquid is retained in the elongation-annealing temperature zone can each be suitably determined according to the target gene regions (e.g., the type of genes and the length of gene regions). For example, the period of time during which the sample liquid is retained in the denaturation temperature zone can be about 2 to 10 seconds, and the period of time during which the sample liquid is retained in the elongation-annealing temperature zone can be about 2 to 60 seconds.

The liquid delivery mechanism is connected to the microchannel through, for example, a connector.

In an embodiment of the present invention, two liquid delivery mechanisms are connected to the microchannel, one mechanism to one end and the other mechanism to the other end of the microchannel. Specifically, a first liquid delivery mechanism connected so as to deliver liquid from the elongation-annealing temperature zone to the denaturation temperature zone is operated in step [1] above, and a second liquid delivery mechanism connected so as to deliver liquid from the denaturation temperature zone to the elongation-annealing temperature zone is operated in step [3] above.

In another embodiment of the present invention, a single liquid delivery mechanism is connected to both ends of the microchannel through a branched connection channel provided with a switching valve. Specifically, in step [1], the liquid delivery mechanism is operated with the channel structured by the switching valve such that liquid is delivered from the elongation-annealing temperature zone to the denaturation temperature zone. In step [3], the liquid delivery mechanism is operated with the channel structured such that liquid is delivered through the switching valve from the denaturation temperature zone to the elongation-annealing temperature zone. If the switching valve is a 3-way valve, the 3-way valve is connected to a microblower or a fan that is open to atmospheric pressure when liquid delivery is stopped. The sample liquid can be reciprocated through the microchannel by alternately blowing air to two connection channels leading to the two ends of the microchannel through two 3-way valves located at both ends of the air channel divided into two directions at the branching point. In this case, a 3-way valve blows air with one mouth closed, and the remaining mouth is open to allow the sample liquid to flow.

In another embodiment of the present invention, two liquid delivery mechanisms (an air ejection means and an air suction means) are connected to one end of the microchannel (at the elongation-annealing temperature zone side) through a branched connection channel provided with a switching valve. Specifically, in step [1], the liquid delivery mechanism (air ejection means) is operated so as to deliver liquid from the elongation-annealing temperature zone toward the denaturation temperature zone through a switching valve. In step [3], the liquid delivery mechanism (air suction means) is operated so as to deliver liquid from the denaturation temperature zone toward the elongation-annealing temperature zone through the switching valve.

In the nucleic acid amplification method according to the present invention in a typical embodiment, the fluorescence intensity of the sample liquid of each thermal cycle is measured at a predetermined point on at least two channels among the three channels: the channel corresponding to the denaturation temperature zone; the channel corresponding to the elongation-annealing temperature zone; and the linear or curved intermediate channel. For example, in an embodiment of the present invention, the fluorescence intensity of the sample liquid of each thermal cycle is measured at a predetermined point on the channel corresponding to the denaturation temperature zone and at a predetermined point on the channel corresponding to the elongation-annealing temperature zone, and optionally at a predetermined point on the linear or curved intermediate channel. The predetermined point on the channel corresponding to the denaturation temperature zone is not particularly limited. However, the predetermined point is preferably the position after one to several (2 to 4) turns or curved portions from the intermediate channel, for example, P1 in FIG. 3. The predetermined point on the channel corresponding to the elongation-annealing temperature zone is not particularly limited. However, the predetermined point is preferably the position after one to several (2 to 4) turns or curved portions from the intermediate channel, for example, P3 in FIG. 3. The predetermined point on the linear intermediate channel is not particularly limited, and may be P2 in FIG. 3. The measurement of the fluorescence intensity of each thermal cycle enables real-time PCR as described above.

If the fluorescence intensity is measured at two points, the points at which the fluorescence intensity is measured can also be a point on the channel corresponding to the elongation-annealing temperature zone, and a point on the linear or curved intermediate channel.

If the fluorescence intensity is measured at three points, the points at which the fluorescence intensity is measured are a point on the channel corresponding to the denaturation temperature zone, a point on the channel corresponding to the elongation-annealing temperature zone, and a point on the linear or curved intermediate channel.

The detection of the fluorescence intensity at one point is preferably of one fluorescence species (one wavelength).

At least one of the measurements of the fluorescence intensity is preferably for detection of the movement of the sample liquid, in addition to monitoring of the status of gene amplification during a PCR reaction. For example, the movement of the sample liquid can be detected in the denaturation temperature zone and in the elongation-annealing temperature zone, and the drive of the liquid delivery mechanism can be controlled by an electric signal related to the movement of the sample liquid emitted from the fluorescence detector.

An example of the control of sample liquid delivery is shown below.

[1] The step of turning on a light source (LED) that illuminates the channel of the denaturation temperature zone, and moving the sample liquid by the liquid delivery mechanism from the elongation-annealing temperature zone to the denaturation temperature zone through the intermediate channel,

[2] The step of receiving in a control mechanism an electric signal that indicates the detection of the sample liquid in the denaturation temperature zone from a fluorescence detector and stopping the liquid delivery mechanism,

[3] The step of turning on a light source (LED) that illuminates the channel of the elongation-annealing temperature zone, and moving the sample liquid by the liquid delivery mechanism from the denaturation temperature zone to the elongation-annealing temperature zone through the intermediate channel, and

[4] The step of receiving in the control mechanism an electric signal that indicates the detection of the sample liquid in the elongation-annealing temperature zone from the fluorescence detector, and stopping the liquid delivery mechanism.

The fluorescence intensity can be measured by detecting the emitted light (fluorescence) generated due to the excitation light irradiated from a light source toward the sample liquid in the microchannel with a fluorescence detector. In measuring the fluorescence intensity in the intermediate channel, it is preferable to measure the fluorescence intensity from the point in time at which the sample liquid begins to pass through the fluorescence intensity detection point (P2) on the intermediate channel to the point in time at which the sample liquid passes through the fluorescence intensity detection point (P1 or P3) on the denaturation or elongation-annealing temperature zone. The obtained measurement results can be stable with less noise by specifying the measurement time (period) of the fluorescence intensity as described above, compared to the results obtained by measuring the fluorescence intensity even after the sample liquid has passed through P1 or P3.

The nucleic acid amplification method according to the present invention can be performed, for example, by using the combination of a nucleic acid amplification device and a chip for nucleic acid amplification described below.

Nucleic Acid Amplification Device

A reciprocal-flow-type nucleic acid amplification device comprising
- a heater to form a denaturation temperature zone and an elongation-annealing temperature zone,
- a fluorescence detector to measure the fluorescence intensity of a sample liquid present in the denaturation temperature zone,
- a fluorescence detector to measure the fluorescence intensity of a sample liquid present in the elongation-annealing temperature zone,
- a liquid delivery mechanism to enable the sample liquid to move between the two temperature zones, and to become open to atmospheric pressure when liquid delivery stops,
- a substrate on which a chip for nucleic acid amplification is mountable, and
- a control mechanism to receive an electric signal indicating the movement of the sample liquid from the fluorescence detector and to control the drive of the liquid delivery mechanism,
- the reciprocal-flow-type nucleic acid amplification device performing real-time PCR by measuring the fluorescence intensity for each thermal cycle.

Chip for Nucleic Acid Amplification

A chip for nucleic acid amplification comprising
at least one microchannel comprising
- a curved channel corresponding to a denaturation temperature zone,
- a curved channel corresponding to an elongation-annealing temperature zone,
- a linear or curved intermediate channel that connects the curved channels, and
- a connector to connect a liquid delivery mechanism of a nucleic acid amplification device to one or both ends of the microchannel.

Specifically, the nucleic acid amplification method according to the present invention can be performed by the following steps 1 to 4:

Step 1: mounting a chip for nucleic acid amplification on a substrate in a nucleic acid amplification device, Step 2: connecting a connector for a liquid delivery mechanism at one or both ends of a microchannel to the liquid delivery mechanism, Step 3: allowing a sample liquid to reciprocate between two curved channels of the microchannel by the liquid delivery mechanism to perform thermal cycling, and Step 4: measuring the fluorescence intensity of the sample liquid for each thermal cycle by using a fluorescence detector at a predetermined point on the channel corresponding to the denaturation temperature zone and at a predetermined point on the channel corresponding to the elongation-annealing temperature zone.

An example of the nucleic acid amplification device and the chip for nucleic acid amplification are described below with reference to figures.

Figure 2:
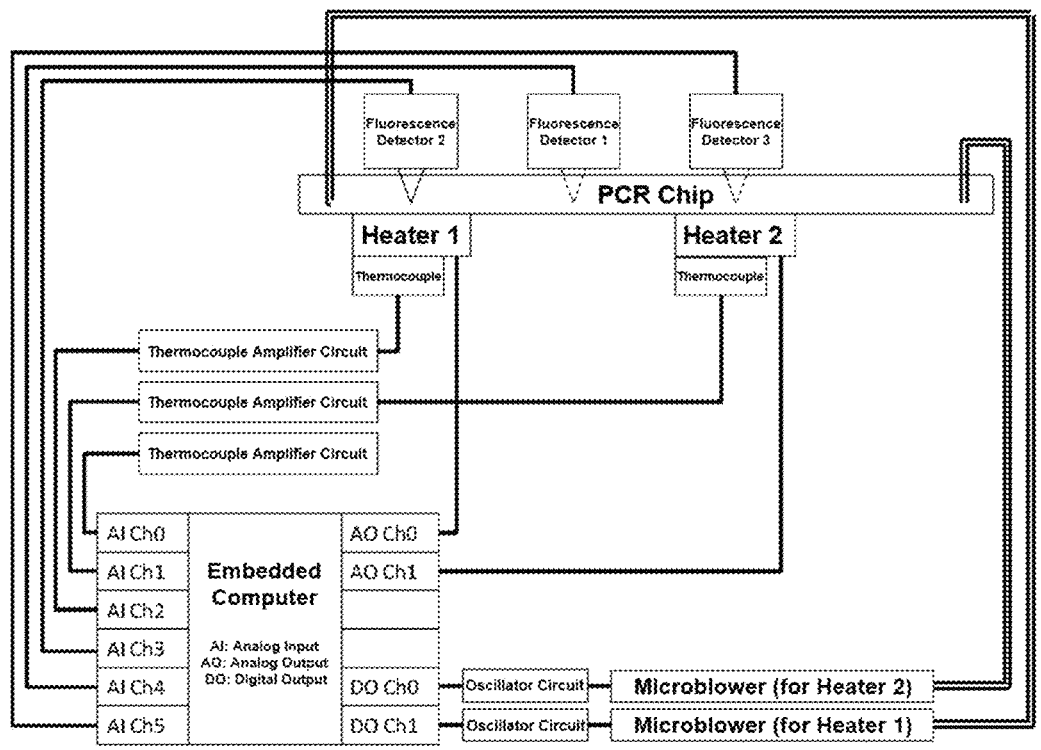
FIG. 2 shows an example of the structure of a nucleic acid amplification device (three heaters).

As shown in FIG. 1, the nucleic acid amplification device can include a substrate (not shown) on which a chip for nucleic acid amplification is mounted, a temperature control unit for the chip for nucleic acid amplification, a liquid delivery mechanism (microblowers are shown as an example), a fluorescence detector, and a compact battery for the power supply of a control computer as a control mechanism.

In FIG. 1, the temperature control unit for the chip for nucleic acid amplification includes two cartridge heaters that are arranged in parallel, 10 mm apart, so as to come in contact with the sealed surfaces of the two curved channels of the chip for nucleic acid amplification. To control the temperature of the two heaters, a Type K thermocouple is bonded to each heater.

Cartridge heater 1 is controlled to a temperature required in a DNA denaturation reaction by the control computer. Cartridge heater 2 is controlled to a temperature required in an annealing reaction and an elongation reaction of DNA by the control computer. The temperature zone for DNA denaturation reaction and the temperature zone for annealing reaction and elongation reaction, for example, can be maintained at a constant temperature by PID (proportional-integral-derivative) control.

The fluorescence detector is disposed to measure the fluorescence intensity at one point on the linear channel of the microchannel of the denaturation temperature zone, at one point on the linear channel of the microchannel of the elongation-annealing temperature zone (P1 and P3 in FIG. 3), and at one point on the intermediate channel (P2 in FIG. 3) as detection points. At the point in time at which the sample liquid delivered from one of the curved channels reaches detection point P1 or P3 due to application of pressure, or immediately after that time point, the liquid delivery mechanism can be stopped to allow the other curved channel to retain the sample liquid for a predetermined period of time.

The control computer is capable of programmed control of the liquid delivery mechanism. While continuously monitoring the fluorescence intensity at the above detection points at the center of each microchannel, the control computer performs thermal cycling by alternately switching the liquid delivery mechanism so that the sample liquid moves alternately toward each curved channel located on the heaters for a set period of time. The control computer also simultaneously records the change in fluorescence intensity for each cycle that increases as the target DNA is amplified by thermal cycling in real-time PCR, and calculates the number of cycles at which the fluorescence intensity exceeds a predetermined threshold (Ct value) to quantify the initial amount of target DNA.

Figure 3:
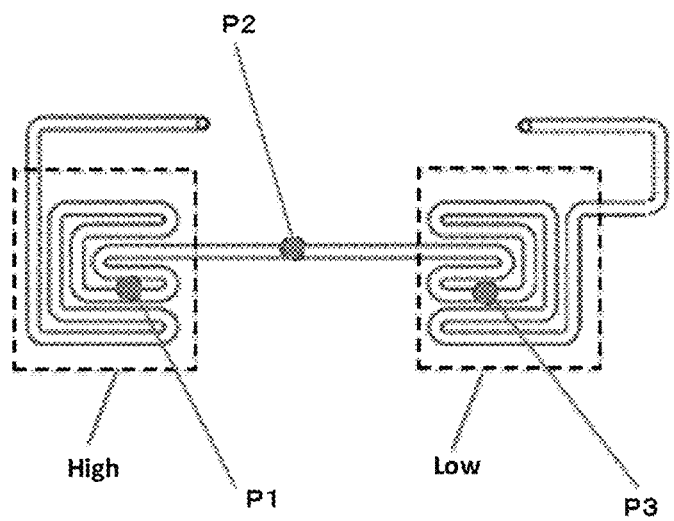
FIG. 3 shows an example of curved channels of a denaturation temperature zone and an elongation-annealing temperature zone, and a linear intermediate channel that connects these curved channels in a PCR chip.

FIG. 3 shows a chip for nucleic acid amplification equipped with a microchannel. In the chip for nucleic acid amplification shown in FIG. 3, two curved channels (serpentine channels), one corresponding to the denaturation temperature zone and the other corresponding to the elongation-annealing temperature zone, are connected by a linear intermediate channel; and the fluorescence of the sample liquid is detected at detection points P1, P2, and P3.

EXAMPLES

The present invention is described below in more detail with reference to Examples. However, the present invention is not limited to the Examples.

Example: Quantification of Pneumonia-Causing-Bacteria Group

Target genes of pneumonia-causing-bacteria group (*Streptococcus pneumoniae, Haemophilus influenzae, Mycoplasma pneumoniae*) were quantified by using a PCR chip for high-speed real-time PCR and the device according to the present invention. The template DNA for *Streptococcus pneumoniae, Haemophilus influenzae*, and *Mycoplasma pneumoniae* for use was AmpliRun (registered trademark) *Streptococcus pneumoniae* DNA control, AmpliRun (registered trademark) *Haemophilus* DNA control, and AmpliRun (registered trademark) *Mycoplasma pneumoniae* DNA control, which are commercially available control DNA. For negative control (NTC), sterile water was instead mixed. High-speed real-time PCR was performed by using them.

The primers and probes of the following sequences were used for three different targets. For *Streptococcus pneumoniae*, the forward primer sequence was 5'-AACTCTTACGCAATCTAGCAGATGAA-3' (SEQ ID NO: 1), the reverse primer sequence was 5'-CGTGCAATACTCGTGCGTTTTA-3' (SEQ ID NO: 2), and the TaqMan (registered trademark) probe sequence was 5'-CCGAAAACGCTTGATACA-3' (SEQ ID NO: 3). For *Haemophilus influenzae*, the forward primer sequence was 5'-GGAATCCCAATGCACAAGAACA-3' (SEQ ID NO. 4), the reverse primer sequence was 5'-GCTTTG GTCAACA-CATCAACCTT-3' (SEQ ID NO. 5), and the TaqMan (registered trademark) probe sequence was 5'-CATTATT-AGTTGCAGGTTCT-3' (SEQ ID NO. 6). For *Mycoplasma pneumoniae*, the forward primer sequence was 5'-CTTGGTCTCCATACTTAACTAAATAAAAAACTC-3' (SEQ ID NO. 7), the reverse primer sequence was 5'-GAACTACAAGCCGCTAATGCAG-3' (SEQ ID NO. 8), and the TaqMan (registered trademark) probe sequence was 5'-GCCTTGAAGGCTGGGTTTGCGCTA-3' (SEQ ID NO. 9).

The fluorescence probes for *Streptococcus pneumoniae, Haemophilus influenzae*, and *Mycoplasma pneumoniae* were respectively Cy5-labeled, FAM-labeled, and ABY-labeled TaqMan (registered trademark) probes. The final concentration of each fluorescence probe in the PCR solution was 200 nM.

The final concentration of each of the forward primers and the final concentration of each of the reverse primers for *Streptococcus pneumoniae* and *Haemophilus influenzae* in the PCR solution was 1.5 µM. The final concentration of the forward primer and the final concentration of the reverse primer for *Mycoplasma pneumoniae* in the PCR solution was 2.0 µM. With regards to other reagents, SpeedSTAR (registered trademark) HS DNA polymerase (Takara Bio Inc.) with a final concentration of 0.15 U/µL was used. Attached FAST Buffer I and dNTP Mixture were mixed in a concentration as instructed in the manual, and prepared as a premixture for PCR.

The 3 types of control DNA were prepared in an amount of $5.0 \times 10^3$ copies/µL. 2 µl each of the 3 types of control DNA or 6 µl of sterile water as NTC was added to 11 µl of the premixture for PCR, and the total amount of 20 µl was used in real-time multiplex PCR.

Thermal cycle conditions were set to perform the following: heating at 98° C. for 10 seconds for hot start, and then further heating 50 cycles at 98° C. for 2 seconds and at 62° C. for 6 seconds. The period of time for 50 cycles of this thermal cycling under these conditions was 8 minutes and 54 seconds.

The light source (LED) that illuminates the channel for the denaturation temperature zone (P1 in FIG. 3) had a wavelength of 525 nm, the light source (LED) that illuminates the intermediate channel (P2 in FIG. 3) had a wavelength of 470 nm, and the light source (LED) that illuminates the channel for the elongation-annealing temperature zone (P3 in FIG. 3) had a wavelength of 630 nm.

Figure 4:
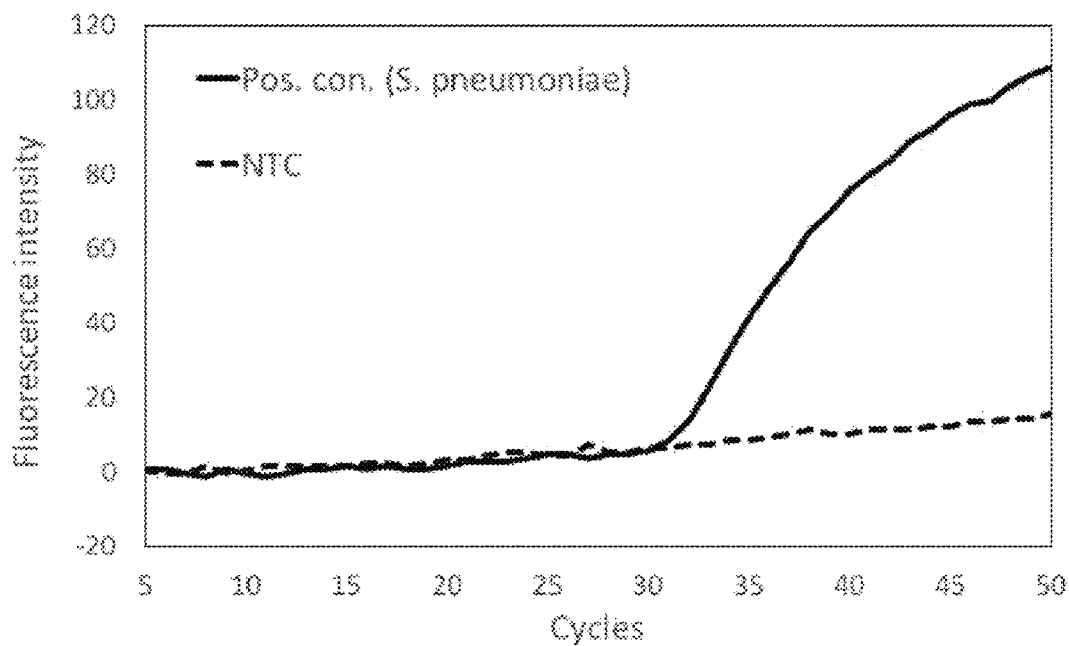
FIG. 4 is a graph of multiplex qPCR (Cy5 detection).
Figure 5:
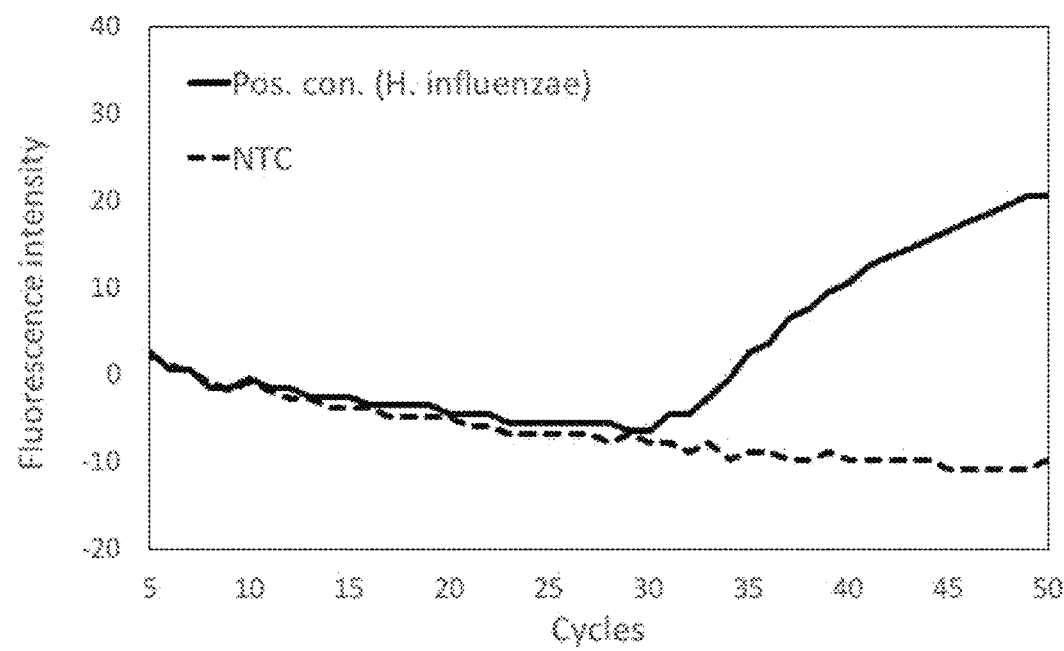
FIG. 5 is a graph of multiplex qPCR (FAM detection).
Figure 6:
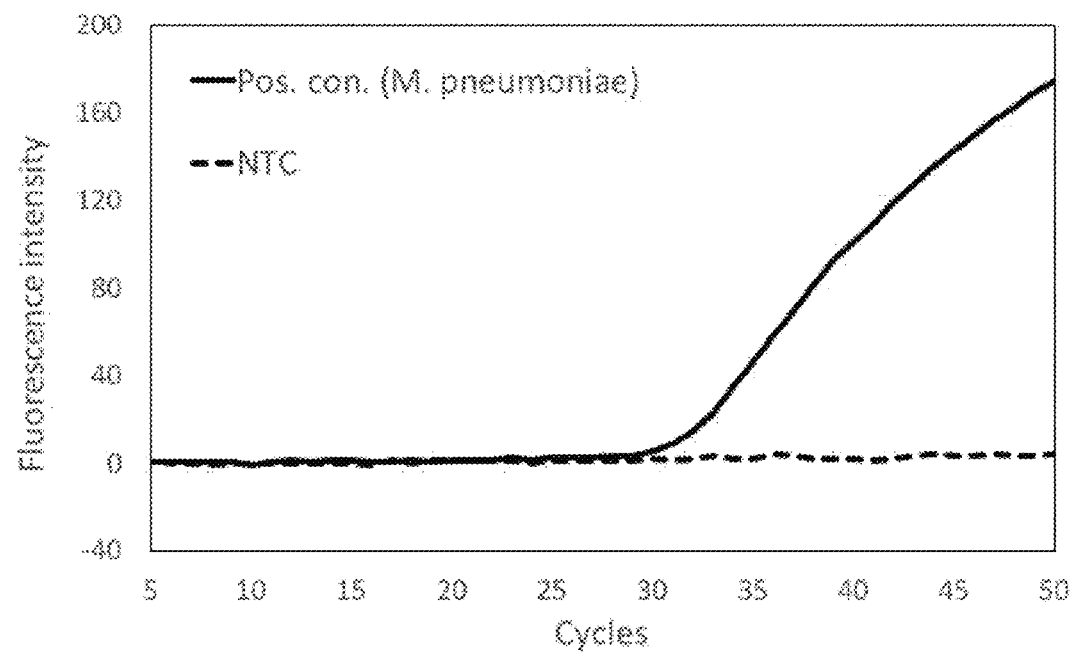
FIG. 6 is a graph of multiplex qPCR (ABY detection).

FIGS. 4 to 6 show the results of multiplex PCR using high-speed real-time PCR on *Streptococcus pneumoniae, Haemophilus influenzae*, and *Mycoplasma pneumoniae*. FIG. 4 shows a change in the fluorescence intensity of Cy5-labeled TaqMan (registered trademark) probe by a solid line as an amplification curve of *Streptococcus pneumoniae* with the results of NTC by a dashed line. FIG. 5 shows a change in the fluorescence intensity of FAM-labeled TaqMan (registered trademark) probe by a solid line as an amplification curve of *Haemophilus influenzae* with the results of NTC by a dashed line. FIG. 6 shows a change in the fluorescence intensity of ABY-labeled TaqMan (registered trademark) probe by a solid line as an amplification curve of *Mycoplasma pneumoniae* with the results of NTC by a dashed line.

As indicated by the solid lines, when any of the three types of control DNA was contained, clear amplification was achieved compared with the amplification shown by the fluorescence signal of NTC indicated by the dashed lines. This indicates that multiple items of the same sample were simultaneously measured.

Sequence Table
P20-06 0WOPCT nucleic acid amplification method_20200313_144223_0.txt

The invention claimed is:

1. A reciprocal-flow-type nucleic acid amplification method performing thermal cycling, the method comprising
moving a sample liquid in a microchannel by a liquid delivery mechanism that is open to atmospheric pressure when liquid delivery is stopped, wherein the microchannel includes at least a curved channel corresponding to a denaturation temperature zone, a curved channel corresponding to an elongation-annealing temperature zone, a linear or curved intermediate channel that connects the curved channel corresponding to the denaturation temperature zone and the curved channel corresponding to the elongation-annealing temperature zone, and a connector connectable to the liquid delivery mechanism for enabling movement of the sample liquid, and
measuring fluorescence intensities for each thermal cycle at a predetermined point on the curved channel corresponding to the denaturation temperature zone and at a predetermined point on the curved channel corresponding to the elongation-annealing temperature zone to perform real-time PCR, wherein the predetermined point on the curved channel corresponding to the denaturation temperature zone is the position after one to four turns or curved portions from the intermediate channel, and the predetermined point on the curved channel corresponding to the elongation-annealing temperature zone is the position after one to four turns or curved portions from the intermediate channel.

2. A nucleic acid amplification method comprising the following steps:
step 1 of mounting a chip for nucleic acid amplification on a substrate of a reciprocal-flow-type nucleic acid amplification device being capable of performing real-time PCR by measuring fluorescence intensity for each thermal cycle, the reciprocal-flow-type nucleic acid amplification device including a heater to form a denaturation temperature zone and an elongation-annealing temperature zone, a fluorescence detector to measure a fluorescence intensity of a sample liquid present in the denaturation temperature zone, a fluorescence detector to measure a fluorescence intensity of the sample liquid present in the elongation-annealing temperature zone, a liquid delivery mechanism to allow the sample liquid to move between the denaturation temperature zone and the elongation-annealing temperature zone, and to become open to atmospheric pressure when liquid delivery is stopped, the substrate on which the chip for nucleic acid amplification is mounted, and a control mechanism to receive an electric signal related to the movement of the sample liquid from the fluorescence detector and control the drive of the liquid delivery mechanism,
the chip for nucleic acid amplification including at least one microchannel, the at least one microchannel including a curved channel corresponding to the denaturation temperature zone, a curved channel corresponding to the elongation-annealing temperature zone, a linear or curved intermediate channel that connects the curved channel corresponding to the denaturation temperature zone and the curved channel corresponding to the elongation-annealing temperature zone, and a connector to connect the liquid delivery mechanism of the nucleic acid amplification device to one or both ends of the microchannel;
step 2 of connecting the connector for the liquid delivery mechanism in the microchannel to the liquid delivery mechanism;
step 3 of reciprocating the sample liquid between the two curved channels in the microchannel by the liquid delivery mechanism to perform thermal cycling; and
step 4 of measuring fluorescence intensities of the sample liquid for each thermal cycle at a predetermined point on the curved channel corresponding to the denaturation temperature zone and at a predetermined point on the curved channel corresponding to the elongation-annealing temperature zone by the fluorescence detectors.

3. The nucleic acid amplification method according to claim 1, wherein the liquid delivery mechanism is a microblower or fan.

4. The nucleic acid amplification method according to claim 1, wherein the intermediate channel that connects the curved channels is a linear channel.

5. The nucleic acid amplification method according to claim 4, the method comprising a step of measuring a fluorescence intensity of the sample liquid for each thermal cycle at a predetermined point on the intermediate channel.

6. A reciprocal-flow-type nucleic acid amplification method performing thermal cycling, the method comprising
moving a sample liquid in a microchannel by a liquid delivery mechanism that is open to atmospheric pressure when liquid delivery is stopped wherein the microchannel includes at least a curved channel corresponding to a denaturation temperature zone, a curved channel corresponding to an elongation-annealing temperature zone, a linear intermediate channel that connects the curved channel corresponding to the denaturation temperature zone and the curved channel corresponding to the elongation-annealing temperature zone, and a connector connectable to the liquid delivery mechanism for enabling movement of the sample liquid, and
measuring fluorescence intensities for each thermal cycle at a predetermined point on the curved channel corresponding to the denaturation temperature zone and at a predetermined point on the curved channel corresponding to the elongation-annealing temperature zone to perform real-time PCR, wherein a distance between a fluorescence measurement point on the intermediate channel and a fluorescence measurement point on the denaturation temperature zone is 8 mm or more.

* * * * *